United States Patent [19]

Steinmeyer

[11] Patent Number: 5,056,129
[45] Date of Patent: Oct. 8, 1991

[54] APPARATUS FOR MONITORING X-RAY BEAM ALIGNMENT

[75] Inventor: Peter A. Steinmeyer, Arvada, Colo.

[73] Assignee: The United States of America as represented by the United States Department of Energy, Washington, D.C.

[21] Appl. No.: 406,003

[22] Filed: Sep. 12, 1989

[51] Int. Cl.$^5$ .............................................. A61B 6/08
[52] U.S. Cl. ..................................... 378/705; 378/207
[58] Field of Search ................. 378/204, 205, 207, 161

[56] References Cited

U.S. PATENT DOCUMENTS

| | | | |
|---|---|---|---|
| 3,538,369 | 11/1970 | Betchen et al. | 313/93 |
| 3,894,230 | 7/1985 | Rorden et al. | 250/208.2 |
| 3,935,450 | 1/1976 | Spugeon | 378/205 |
| 4,409,485 | 10/1983 | Morris et al. | 250/374 |
| 4,532,646 | 7/1985 | Gilbert | 378/207 |
| 4,596,933 | 6/1986 | Waechter et al. | 250/388 |
| 4,633,089 | 12/1986 | Wijangco | 250/374 |
| 4,707,607 | 11/1987 | Whetten | 250/385 |
| 4,862,489 | 8/1989 | Appelt | 378/117 |

OTHER PUBLICATIONS

"X-α,β-Ray Detector Windows . . . Replacing Beryllium" . . . , by Rimbert et al., Nuc. Inst. and Methods in Physics Research, 1986, pp. 95–100.

Primary Examiner—Carolyn E. Fields
Assistant Examiner—David P. Porta
Attorney, Agent, or Firm—Anne D. Daniel; James H. Chafin; William R. Moser

[57] ABSTRACT

A self-contained, hand-held apparatus is provided for minitoring alignment of an X-ray beam in an instrument employing an X-ray source. The apparatus includes a transducer assembly containing a photoresistor for providing a range of electrical signals responsive to a range of X-ray beam intensities from the X-ray beam being aligned. A circuit, powered by a 7.5 VDC power supply and containing an audio frequency pulse generator whose frequency varies with the resistance of the photoresistor, is provided for generating a range of audible sounds. A portion of the audible range corresponds to low X-ray beam intensity. Another portion of the audible range corresponds to high X-ray beam intensity. The transducer assembly may include an a photoresistor, a thin layer of X-ray fluorescent material, and a filter layer transparent to X-rays but opaque to visible light. X-rays from the beam undergoing alignment penetrate the filter layer and excite the layer of fluorescent material. The light emitted from the fluorescent material alters the resistance of the photoresistor which is in the electrical circuit including the audio pulse generator and a speaker. In employing the apparatus, the X-ray beam is aligned to a complete alignment by adjusting the X-ray beam to produce an audible sound of the maximum frequency.

9 Claims, 1 Drawing Sheet

APPARATUS FOR MONITORING X-RAY BEAM ALIGNMENT

The United States Government has rights in this invention pursuant to Contract No. DE-AC04-76DP03533 between the United States Department of Energy and Rockwell International Corporation.

BACKGROUND OF THE INVENTION

The present invention relates to the field of monitoring X-ray beams, and more particularly to monitoring an X-ray beam for alignment of X-ray diffraction and X-ray fluorescent equipment.

In the art of aligning an X-ray beam in X-ray diffraction and X-ray fluorescent equipment, a hand-held fluorescent screen device is commonly used. In practice, the use of the hand-held fluorescent screen requires that the X-ray beam intensity be relatively high. Also, the use of the hand-held screen often requires that the room lights be dimmed. The relatively high intensity X-ray beam and the necessity to dim room lights are especially required when finely collimated X-ray beams are used, as in the case of microdiffractometry.

In the art of measuring ambient radiation, the use of Geiger counters is well known. Generally, a Geiger counter employs a relatively high voltage (e.g. 1,000 volts) to provide ionization in a chamber. An audible output often accompanies the monitoring of the radiation. Yet for the purpose of aligning an X-ray beam, the Geiger counter is not desirable. It would be desirable, however, to provide an apparatus for monitoring the alignment of an X-ray beam without requiring a high voltage and without requiring an ionization chamber.

SUMMARY OF THE INVENTION

Accordingly, an object of the present invention to provide an apparatus for monitoring the alignment of an X-ray beam which can be employed with a relatively low intensity X-ray beam.

Another object of the invention is to provide apparatus for monitoring the alignment of an X-ray beam which does not require dimming of room lights for use.

Another object is to provide a hand-held apparatus for monitoring the alignment of an X-ray beam without requiring a high voltage and without requiring an ionization chamber.

Additional objects, advantages, and novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

To achieve the foregoing and other objects, and in accordance with the purposes of the present invention as described herein, an improved apparatus is provided for monitoring alignment of an X-ray beam in an instrument employing an X-ray source. The apparatus includes means for providing an electrical signal responsive to X-ray beam intensity during alignment of the X-ray beam. Also provided are means, responsive to the electrical signalling means, for generating an audible sound when the X-ray beam is aligned to the desired alignment. More specifically, the desired alignment is obtained by an operator adjusting the X-ray beam and listening for the audible sound that indicates that the desired alignment has been obtained.

In a preferred embodiment, the apparatus includes means for providing a range of electrical signals responsive to a range of X-ray beam intensities from the X-ray source. Means, responsive to the electrical signalling means, are also provided for generating a range of audible sounds. A portion of the audible range corresponds to low X-ray beam intensity. Another portion of the audible range corresponds to high X-ray beam intensity. In employing the apparatus, the X-ray beam is aligned to a desired alignment by adjusting the X-ray beam to produce an audible sound corresponding to a desired X-ray beam intensity.

More specifically, the electrical signalling means may be comprised of an assembly which includes a photoresistor, a thin layer of X-ray fluorescent material, and a filter layer transparent to X-rays but opaque to visible light. X-rays from the beam undergoing alignment penetrate the filter layer and excite the layer of fluorescent material. The light emitted from the fluorescent material alters the resistance of a photoresistor which is in an electrical circuit with an audio pulse generator and a speaker. By monitoring the frequency of the audible sounds emitted, the X-ray beam is adjusted to produce a sound corresponding to a desired X-ray beam intensity.

The apparatus of the invention is self-contained, small and compact, and can be a hand-held apparatus.

Still other objects of the present invention will become readily apparent to those skilled in this art from the following description, wherein there is shown and described a preferred embodiment of this invention. Simply by way of illustration, the invention will be set forth in part in the description that follows and in part will become apparent to those skilled in the art upon examination of the following or may be learned with the practice of the invention. Accordingly, the drawings and descriptions will be regarded as illustrative in nature and not as restrictive.

BRIEF DESCRIPTION OF THE DRAWINGS

The accompanying drawings incorporated in and forming a part of the specification, illustrate several aspects of the present invention, and together with the description serve to explain the principles of the invention. In the drawings.

DETAILED DESCRIPTION

Figure 1:
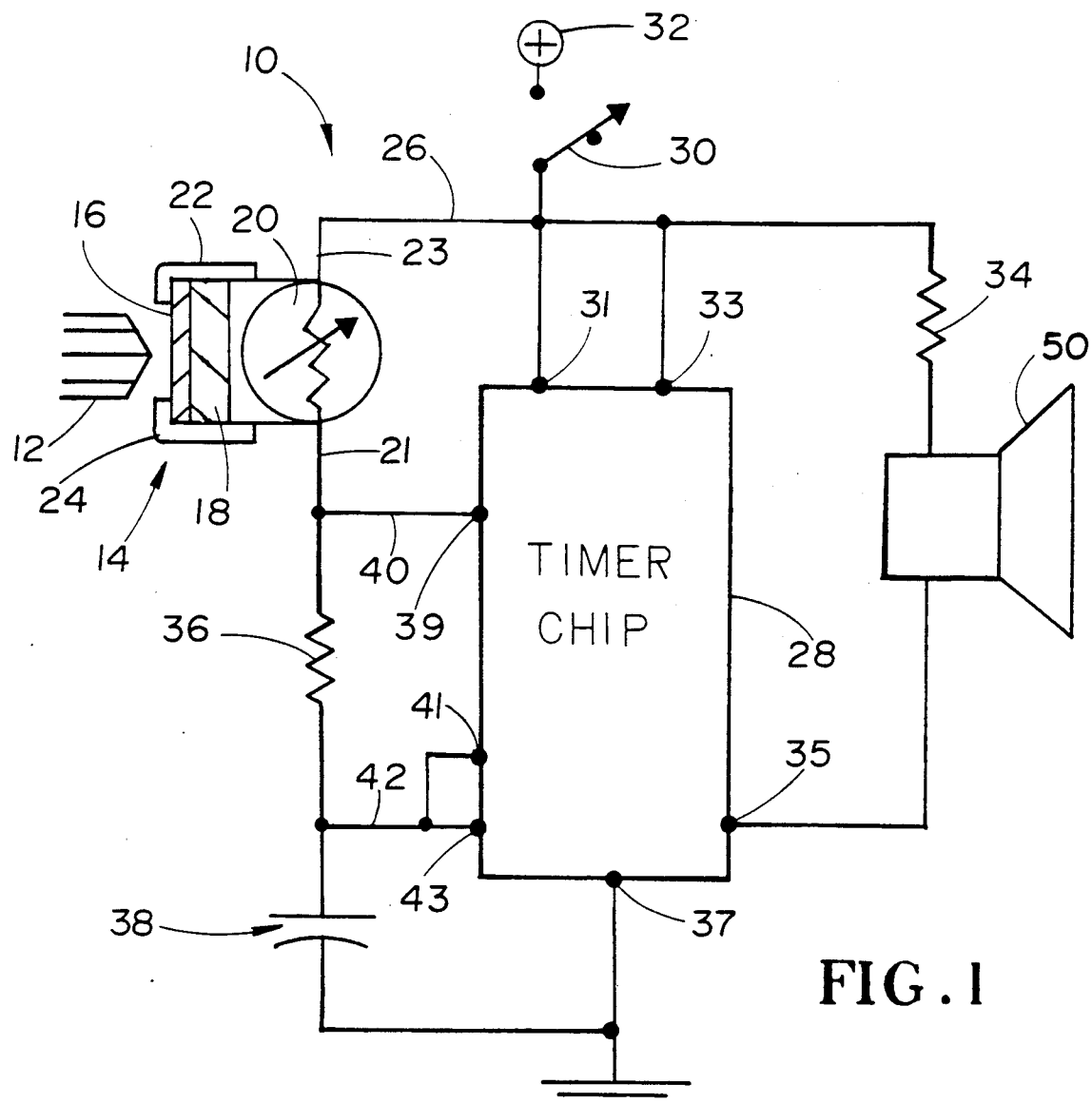
FIG. 1 is a circuit diagram including a photoresistor, an audio frequency pulse generator responsive to the resistance of the photoresistor, and a speaker responsive to the pulse generator.

With reference to the drawings, and more particularly to FIG. 1, an embodiment of the X-ray beam alignment apparatus 10 is disclosed. An X-ray beam 12 is directed to a transducer assembly 14 which includes a 0.005 inch filter layer of beryllium foil 16, a 0.003 inch layer 18 of zinc sulfide fluorescent material adjacent to the filter layer 16, and a photoresistor 20 underlying the fluorescent layer. Tapes 22 and 24 are formed from the chemical element Lead (Pb). The lead tapes 22 and 24 are opaque to visible and X-ray radiation and are placed at the edges of the filter layer 16, the fluorescent layer 18, and the photoresistor 20 to prevent ambient light from reaching the photoresistor 20. The filter layer 16 serves to pass X-rays to excite fluorescence and to block other wavelengths of electromagnetic radiation from causing fluorescence.

The photoresistor 20 is an element in an electrical circuit which continuously varies audible sound emitted from a speaker 50 as the resistance of photoresistor 20 varies. More specifically, one electrical lead 23 of photoresistor 20 is connected to conductor 26 which is connected to standard integrated circuit type 555 timer chip 28 by conductors at pin 4 (reference numeral 31) and pin 8 (reference numeral 33) of timer chip 28. Switch 30, shown in the "off" position in FIG. 1, connects the entire circuit to a 7.5 volt DC power supply, depicted by positive post 32, which provides 5 mA of current.

Conductor 26 is also connected in series with 180 ohm dropping resistor 34, with 8 ohm/3 inch speaker 50, and with pin 3 (reference numeral 35) of the timer chip 28. Pin 1 (reference numeral 37) of the timer chip 28 is connected to ground.

An RC circuit is present as part of the circuit in FIG. 1. More specifically, 1000 ohm resistor 36 is connected in series the photoresistor 20, with lead 21, and with a 0.1 microfarad capacitor 38 which is connected to ground. Pin 7 (reference numeral 39) of the timer chip 28 is connected by conductor 40 between the lead 21 and the resistor 36. Pin 6 (reference numeral 41) of the timer chip 28 is shunted to pin 2 (reference numeral 43) which is connected by conductor 42 between resistor 36 and capacitor 38.

The circuit shown in FIG. 1 is a simple audio frequency pulse generator whose frequency varies with the resistance of the photoresistor 20, which in turn varies with the X-ray flux incident on the face of the transducer assembly 14.

All the circuit elements in FIG. 1 and the transducer assembly 14 and the power supply can be arranged in a self-contained, small, compact, hand-held unit.

In operation of the audio frequency generator circuit shown in FIG. 1, the photoresistor 20 is responsive to the light emitted by the fluorescent layer 18 when excited by the X-ray beam 12. The adjustment of the X-ray beam 12 with respect to the transducer assembly 14 can be calibrated so that the X-ray beam is in complete alignment when the X-ray beam 12 is aimed at the transducer assembly 14 so that essentially the entire X-ray beam 12 impinges upon the filter layer 16. When this occurs, the maximum amount of X-ray energy passes through the filter layer 16, the maximum amount of X-ray energy brings about a maximum amount of fluorescence in layer 18, the photoresistor 20 has minimum resistance, and the timer chip 28 drives the speaker 50 at maximum audible frequency.

In contrast, if the X-ray beam 12 is not in desired alignment, then only a portion of the X-ray beam 12 impinges upon the filter layer 16, and only a portion of the X-ray energy passes through the filter layer 16 to excite the fluorescent layer 18 and bring about a greater than minimum resistance of the photoresistor 20. In such a case, the timer chip 28 drives the speaker 50 at a frequency that is less than the maximum audible frequency.

A continuous audible range exists for the degree of misalignment of the X-ray beam 12. A complete misalignment would result in the X-ray beam 12 missing the transducer assembly 14 completely. This would result in the photoresistor 20 having its highest resistance or dark resistance (approximately one megohm for the photoresistor selected), and the audible frequency produced would be the lowest audible frequency, which is a series of low frequency clicks when the X-ray beam is completely misaligned (for the values of the circuit elements selected for FIG. 1). On the other hand, a complete alignment of the X-ray beam 12 would result in the entire wavefront of the X-ray beam 12 impinging upon the filter layer 16 of the transducer assembly 14 thereby resulting in the photoresistor 20 having its lowest resistance at approximately 200 ohms; and the timer chip 28 would drive the speaker 50 at the maximum audible frequency.

Thus, a person who is aligning the X-ray beam 12 can listen to the audible sounds and make adjustments to the X-ray beam 12 to produce an audible sound in keeping with the desired degree of alignment. More specifically, if a complete misalignment is desired, adjustments to the X-ray beam 12 would be made to produce the lowest frequency clicks. On the other hand, if a complete alignment were desired, adjustments to the X-ray beam would be made to produce the highest frequency sounds. The apparatus of the invention is easily adjusted to correlate the audible frequency with the desired degree of X-ray beam alignment.

Figure 2:
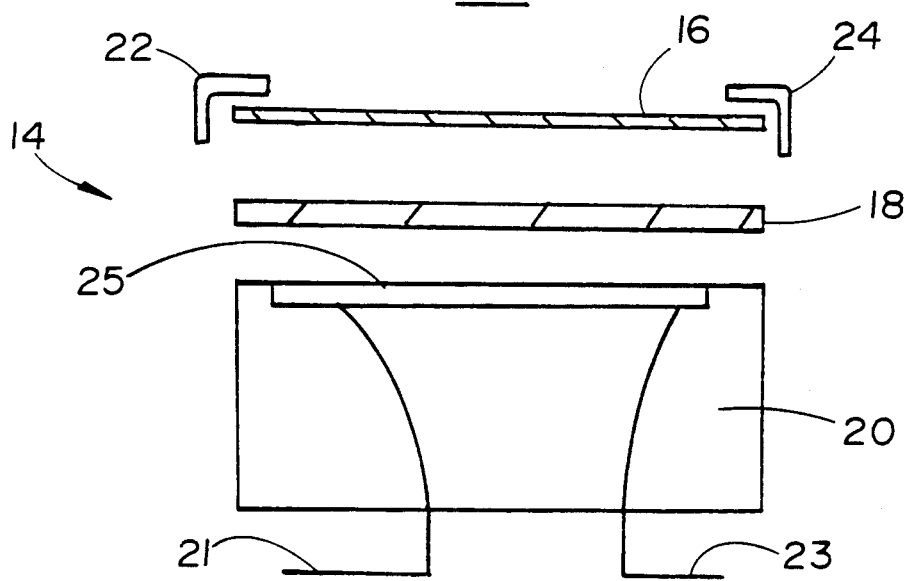
FIG. 2 is an exploded and enlarged schematic diagram of an X-ray transducer assembly shown in FIG. 1 which includes a filter opaque to visible light but transparent to an X-ray beam, a layer of material that fluoresces when excited by X-rays, and the photoresistor.

Turning to FIG. 2, the structures of the transducer assembly 14 are shown in greater detail in an exploded view. Transducer assembly 14 includes a 0.005 inch filter layer of beryllium foil 16, a 0.003 inch layer 18 of zinc sulfide fluorescent material adjacent to the filter layer 16, and a photoresistor 20 underlying the fluorescent layer. Lead (Pb) tapes 22 and 24 (which are opaque to visible and X-ray radiation) are placed at the edges of the filter layer 16, the fluorescent layer 18, and the photoresistor 20 to prevent ambient light from reaching the photoresistor 20. The filter layer 16 serves to pass X-rays to excite fluorescence and to block other wavelengths of electromagnetic radiation from causing fluorescence. Leads 21 and 23 of the photoresistor 20 are connected to opposite ends of the top surface 25 of the photoresistor 20 which contains the photoresistive material of the photoresistor 20.

In summary, numerous benefits have been described which result from employing the principles of the invention. With the invention an apparatus is provided for monitoring the alignment of an X-ray beam which can be employed with a relatively low intensity X-ray beam. The transducer of the invention is highly sensitive to X-rays and is responsive to a relatively low intensity X-ray beam. With the invention, an apparatus is provided for monitoring the alignment of an X-ray beam which does not require dimming of room lights for use. Audible signals are provided for purposes of alignment, and ambient light does not affect the audio signal.

Also by employing the principles of the invention, a self-contained, hand-held apparatus is provided for monitoring the alignment of an X-ray beam without requiring a high voltage source and without requiring an ionization chamber. The transducer assembly includes the photoresistor and operates in the audio frequency generator circuit which is powered by a relatively low voltage (e.g. 7.5 VDC) source.

The foregoing description of the invention has been presented for purposes of illustration and description. It is not intended to be exhaustive or to limit the invention to the precise form disclosed. Obvious modifications or variations are possible in light of the above teachings. For example, although the embodiment disclosed above relates to X-ray beams and the alignment thereof, the principles of the invention can be used for aligning electromagnetic wave beams generally. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed is:

1. An apparatus for monitoring alignment of an X-ray beam, comprising:
   a housing
   means for providing electrical signals responsive to X-ray beam intensities during alignment of the X-ray beam, comprising
   a protective filter layer transparent to X-rays but opaque to visible light, a layer of X-ray fluorescent material, adjacent to said filter layer, and
   a photoresistor in close proximity to said X-ray fluorescent material, for providing variable resistance responsive to said X-ray beam intensities,
   audio frequency generating means, electrically connected to said photoresistor, for generating variable frequencies corresponding to said variable resistance,
   sound generating means, electrically connected to said audio frequency generating means, for generating sounds corresponding to said variable frequencies, and
   low voltage power supply means connected to said monitoring apparatus by a switching means, for enabling said apparatus,
   whereby, by monitoring the frequency of the sounds emitted by said sound generating means, an X-ray beam is aligned to a desired alignment by adjusting the X-ray beam to produce a sound corresponding to a desired X-ray beam intensity.

2. The monitoring apparatus of claim 1, wherein said housing comprises at least one strip of tape placed at the edges of said electrical signalling means.

3. The monitoring apparatus of claim 2, wherein said at least one tape strip is lead.

4. The apparatus described in claim 1, wherein the frequency variation of said audio frequency generating means is proporitonal to the X-ray beam intensity, such that the pitch of the sound produced by said sound generating means varies with the intensity of the X-ray beam.

5. The apparatus described in claim 1 wherein said X-ray fluorescent material is comprised of a layer of zinc sulfide.

6. The apparatus described in claim 1 wherein said filter layer is comprised of a layer of beryllium foil.

7. The apparatus described in claim 1, wherein said audio frequency generating means includes an audio frequency pulse generator whose frequency varies with signals from said electrical signalling means.

8. The apparatus described in claim 1, wherein said low voltage power supply means is a 7.5 volt DC power supply.

9. The apparatus described in claim 1, wherein said housing contains said electrical signalling means, said audio frequency generating means, said sound generating means, and said power supply means, so that the monitoring apparatus is self-contained and dimensioned to be hand-held.

* * * * *